(12) United States Patent
Maffitt et al.

(10) Patent No.: US 6,274,366 B1
(45) Date of Patent: Aug. 14, 2001

(54) ENZYMATICALLY-ACTIVE RECOMBINANT HUMAN β-TRYPTASE AND METHOD OF MAKING SAME

(75) Inventors: Mark A. Maffitt; Andrew L. Niles; Mary Haak-Frendscho, all of Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/079,970

(22) Filed: May 15, 1998

(51) Int. Cl.[7] ............................. C12N 9/50; C12N 15/00; C07H 21/04
(52) U.S. Cl. ..................... 435/226; 435/212; 435/219; 435/252.3; 435/254.11; 435/325; 435/320.1; 536/23.1; 536/23.2
(58) Field of Search .................................. 435/212, 219, 435/226, 252.3, 254.11, 325, 320.1; 536/23.2, 23.1

(56) References Cited

FOREIGN PATENT DOCUMENTS

WO 97/17373    5/1997  (WO) .

OTHER PUBLICATIONS

Niles, A.L. et al. (1998) "The Expression and Characterization of Enzymatically Active Human Mast Cell Tryptase in *P. pastoris*," *FASEB Journal*, 12:A896.

Chan, H. et al. (1996) "Expression of Active Human Mast Cell Tryptase in *Pichia Pastoris*," *FASEB Journal*, 10:A1404.

Schwartz, L.B. (1985) "Monoclonal Antibodies Against Human Mast Cell Tryptase Demonstrate Shared Antigenic Sites on Subunits of Tryptase and Selective Localization of the Enzyme to Mast Cells," *Journal of Immunology*, 134:526–531.

Blom, T. and Hellman L., Characterization of a Tryptase mRNA Expressed in the Human Basophil Cell Line KU812, *Scand. J. Immunol.* (1993), 37:203–208.

Buckholz, R. and Gleeson, M.A.G., Yeast Systems For the Commercial Production of Heterologous Proteins, *Biotechnology* (Nov. 1991) 9:1067–1072.

Ide et al. cDNA Sequencing and Expression of Rat Mast Cell Tryptase, *J. Biochem* (1995), 118:210–215.

Miller, J., et al., Cloning and Characterization of a Second Complementary DNA for Human Tryptase, *J. Clin. Invest.* (1990), 86:864–870.

Nico Faber et al., Review: Methylotrophic Yeasts as Factories for the Production of Foreign Proteins, *Yeast* (1995), 11:1331–1344.

Sakai et al., Expression and Purification of Recombinant Human Tryptase in a Caculovirus System, *Protein Expression and Purification* (1996), 7:67–73.

Smith et al., Human Lung Tryptase, *The Journal of Biological Chemistry* (1984), 259(17):11046–11051.

Vanderslice et al., Human mast cell tryptase: Multiple cDNAs and genes reveal a multigene serine protease family, *Biochemistry* (1990), 87:3811–3815.

Whelan, Kenneth F. and Taylor, Diane E., Antibody Screening for Secreted Proteins Expressed in *Pichia pastoris*, *BioTechniques* (1996), 21:808–812.

Sreekrishna et al., Strategies and secretion of heterologous proteins in the methylotrophic yeast *Pichia pastoris*, *Gene* 190: 55–62, Apr. 1997.*

Vanderslice et al., Human mast cell tryptase: Multiple cDNAs and genes reveal a multigene serine protease family, *Proc. Natl. Acad. Sci. USA* 87:3811–3815, May 1990.*

Invitrogen Catalog, 1997 p 17.*

Matsudaira (1991) Limited N–terminal sequence analysis. *Methods in Enzymology* 182: 602–613, Feb. 1991.*

Wozney et al. (1991) Using purified protein to clone its gene. *Methods in Enzymology* 182: 738–751, Feb. 1991.*

Johnson, D. et al. (1992) "Mast Cell Tryptases: Examination of Unusual Characteristics by Multiple Sequence Alignment and Molecular Modeling," *Protein Science*, 1:370–377.

Miller, J. S. et al. (1989) "Cloning and Characterization of Complementary DNA for Human Tryptase," *J. Clin. Invest.*, 84:1188–1195.

* cited by examiner

*Primary Examiner*—Rebecca E. Prouty
*Assistant Examiner*—Richard Hutson
(74) *Attorney, Agent, or Firm*—Joseph T. Leone, Esq.; DeWitt Ross & Stevens S.C.

(57) ABSTRACT

Disclosed is a method of expressing enzymatically-active, recombinant human β-tryptase in a yeast host cell, expression constructs which drive the production of enzymatically-active tryptase in transformed yeast, and genetically-engineered yeast containing the expression constructs and which express enzymatically-active human β-tryptase. Uses for the tryptase so produced are also disclosed.

13 Claims, 8 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 735 base pairs
      (B) TYPE: nucleic acid
      (C) STRANDEDNESS: single
      (D) TOPOLOGY: linear

```
    (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (ix) FEATURE:
         (A) NAME/KEY: CDS
         (B) LOCATION: 1..735

(xi) SEQUENCE DESCRIPTION: SEQ ID NO:1:

ATC GTC GGG GGT CAG GAG GCC CCC AGG AGC AAG TGG CCC TGG CAG GTG      48
Ile Val Gly Gly Gln Glu Ala Pro Arg Ser Lys Trp Pro Trp Gln Val
  1               5                  10                  15

AGC CTG AGA GTC CAC GGC CCA TAC TGG ATG CAC TTC TGC GGG GGC TCC      96
Ser Leu Arg Val His Gly Pro Tyr Trp Met His Phe Cys Gly Gly Ser
                 20                  25                  30

CTC ATC CAC CCC CAG TGG GTG CTG ACC GCA GCG CAC TGC GTG GGA CCG     144
Leu Ile His Pro Gln Trp Val Leu Thr Ala Ala His Cys Val Gly Pro
             35                  40                  45

GAC GTC AAG GAT CTG GCC GCC CTC AGG GTG CAA CTG CGG GAG CAG CAC     192
Asp Val Lys Asp Leu Ala Ala Leu Arg Val Gln Leu Arg Glu Gln His
 50                  55                  60

CTC TAC TAC CAG GAC CAG CTG CTG CCG GTC AGC AGG ATC ATC GTG CAC     240
Leu Tyr Tyr Gln Asp Gln Leu Leu Pro Val Ser Arg Ile Ile Val His
 65                  70                  75                  80

CCA CAG TTC TAC ACC GCC CAG ATC GGA GCG GAC ATC GCC CTG CTG GAG     288
Pro Gln Phe Tyr Thr Ala Gln Ile Gly Ala Asp Ile Ala Leu Leu Glu
                 85                  90                  95

CTG GAG GAG CCG GTG AAG GTC TCC AGC CAC GTC CAC ACG GTC ACC CTG     336
Leu Glu Glu Pro Val Lys Val Ser Ser His Val His Thr Val Thr Leu
                100                 105                 110

CCC CCT GCC TCA GAG ACC TTC CCC CCG GGG ATG CCG TGC TGG GTC ACT     384
Pro Pro Ala Ser Glu Thr Phe Pro Pro Gly Met Pro Cys Trp Val Thr
            115                 120                 125

GGC TGG GGC GAT GTG GAC AAT GAT GAG CGC CTC CCA CCG CCA TTT CCT     432
Gly Trp Gly Asp Val Asp Asn Asp Glu Arg Leu Pro Pro Pro Phe Pro
        130                 135                 140

CTG AAG CAG GTG AAG GTC CCC ATA ATG GAA AAC CAC ATT TGT GAC GCA     480
Leu Lys Gln Val Lys Val Pro Ile Met Glu Asn His Ile Cys Asp Ala
145                 150                 155                 160

AAA TAC CAC CTT GGC GCC TAC ACG GGA GAC GAC GTC CGC ATC GTC CGT     528
Lys Tyr His Leu Gly Ala Tyr Thr Gly Asp Asp Val Arg Ile Val Arg
                165                 170                 175

GAC GAC ATG CTG TGT GCC GGG AAC ACC CGG AGG GAC TCA TGC CAG GGC     576
Asp Asp Met Leu Cys Ala Gly Asn Thr Arg Arg Asp Ser Cys Gln Gly
            180                 185                 190

GAC TCC GGA GGG CCC CTG GTG TGC AAG GTG AAT GGC ACC TGG CTG CAG     624
Asp Ser Gly Gly Pro Leu Val Cys Lys Val Asn Gly Thr Trp Leu Gln
        195                 200                 205

GCG GGC GTG GTC AGC TGG GGC GAG GGC TGT GCC CAG CCC AAC CGG CCT     672
Ala Gly Val Val Ser Trp Gly Glu Gly Cys Ala Gln Pro Asn Arg Pro
    210                 215                 220

GGC ATC TAC ACC CGT GTC ACC TAC TAC TTG GAC TGG ATC CAC CAC TAT     720
Gly Ile Tyr Thr Arg Val Thr Tyr Tyr Leu Asp Trp Ile His His Tyr
225                 230                 235                 240

GTC CCC AAA AAG CCG                                                  735
Val Pro Lys Lys Pro
                245
```

(2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
CTCGAGAAAA GAATCGTCGG GGGTCAGGAG GCCC                                      34
```

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
TGCTGCCGCC GGCGAAGTGC CGAAAAACCC CTGTATCACC                                40
```

(2) INFORMATION FOR SEQ ID NO:4:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 7..753

(ix) FEATURE:
        (A) NAME/KEY: misc_signal
        (B) LOCATION: 7..18

(xi) SEQUENCE DESCRIPTION: SEQ ID NO:4:

```
GGGCCC CTC GAG AAA AGA ATC GTC GGG GGT CAG GAG GCC CCC AGG AGC            48
       Leu Glu Lys Arg Ile Val Gly Gly Gln Glu Ala Pro Arg Ser
         1               5                  10

AAG TGG CCC TGG CAG GTG AGC CTG AGA GTC CAC GGC CCA TAC TGG ATG           96
Lys Trp Pro Trp Gln Val Ser Leu Arg Val His Gly Pro Tyr Trp Met
 15              20                  25                  30

CAC TTC TGC GGG GGC TCC CTC ATC CAC CCC CAG TGG GTG CTG ACC GCA          144
His Phe Cys Gly Gly Ser Leu Ile His Pro Gln Trp Val Leu Thr Ala
             35                  40                  45
```

```
GCG CAC TGC GTG GGA CCG GAC GTC AAG GAT CTG GCC GCC CTC AGG GTG        192
Ala His Cys Val Gly Pro Asp Val Lys Asp Leu Ala Ala Leu Arg Val
         50                  55                  60

CAA CTG CGG GAG CAG CAC CTC TAC TAC CAG GAC CAG CTG CTG CCG GTC        240
Gln Leu Arg Glu Gln His Leu Tyr Tyr Gln Asp Gln Leu Leu Pro Val
         65                  70                  75

AGC AGG ATC ATC GTG CAC CCA CAG TTC TAC ACC GCC CAG ATC GGA GCG        288
Ser Arg Ile Ile Val His Pro Gln Phe Tyr Thr Ala Gln Ile Gly Ala
         80                  85                  90

GAC ATC GCC CTG CTG GAG CTG GAG GAG CCG GTG AAG GTC TCC AGC CAC        336
Asp Ile Ala Leu Leu Glu Leu Glu Glu Pro Val Lys Val Ser Ser His
 95                 100                 105                 110

GTC CAC ACG GTC ACC CTG CCC CCT GCC TCA GAG ACC TTC CCC CCG GGG        384
Val His Thr Val Thr Leu Pro Pro Ala Ser Glu Thr Phe Pro Pro Gly
                    115                 120                 125

ATG CCG TGC TGG GTC ACT GGC TGG GGC GAT GTG GAC AAT GAT GAG CGC        432
Met Pro Cys Trp Val Thr Gly Trp Gly Asp Val Asp Asn Asp Glu Arg
            130                 135                 140

CTC CCA CCG CCA TTT CCT CTG AAG CAG GTG AAG GTC CCC ATA ATG GAA        480
Leu Pro Pro Pro Phe Pro Leu Lys Gln Val Lys Val Pro Ile Met Glu
            145                 150                 155

AAC CAC ATT TGT GAC GCA AAA TAC CAC CTT GGC GCC TAC ACG GGA GAC        528
Asn His Ile Cys Asp Ala Lys Tyr His Leu Gly Ala Tyr Thr Gly Asp
        160                 165                 170

GAC GTC CGC ATC GTC CGT GAC GAC ATG CTG TGT GCC GGG AAC ACC CGG        576
Asp Val Arg Ile Val Arg Asp Asp Met Leu Cys Ala Gly Asn Thr Arg
175                 180                 185                 190

AGG GAC TCA TGC CAG GGC GAC TCC GGA GGG CCC CTG GTG TGC AAG GTG        624
Arg Asp Ser Cys Gln Gly Asp Ser Gly Gly Pro Leu Val Cys Lys Val
                195                 200                 205

AAT GGC ACC TGG CTG CAG GCG GGC GTG GTC AGC TGG GGC GAG GGC TGT        672
Asn Gly Thr Trp Leu Gln Ala Gly Val Val Ser Trp Gly Glu Gly Cys
            210                 215                 220

GCC CAG CCC AAC CGG CCT GGC ATC TAC ACC CGT GTC ACC TAC TAC TTG        720
Ala Gln Pro Asn Arg Pro Gly Ile Tyr Thr Arg Val Thr Tyr Tyr Leu
            225                 230                 235

GAC TGG ATC CAC CAC TAT GTC CCC AAA AAG CCG TGAAGCGGCC GCCGTCGT        771
Asp Trp Ile His His Tyr Val Pro Lys Lys Pro
    240                 245
```

(2) INFORMATION FOR SEQ ID NO:5:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO:5:

```
Leu Glu Lys Arg Ile Val Gly Gly Gln Glu Ala Pro Arg Ser Lys Trp
 1               5                  10                  15

Pro Trp Gln Val Ser Leu Arg Val His Gly Pro Tyr Trp Met His Phe
            20                  25                  30

Cys Gly Gly Ser Leu Ile His Pro Gln Trp Val Leu Thr Ala Ala His
            35                  40                  45

Cys Val Gly Pro Asp Val Lys Asp Leu Ala Ala Leu Arg Val Gln Leu
    50                  55                  60

Arg Glu Gln His Leu Tyr Tyr Gln Asp Gln Leu Leu Pro Val Ser Arg
 65                 70                  75                  80
```

```
Ile Ile Val His Pro Gln Phe Tyr Thr Ala Gln Ile Gly Ala Asp Ile
                85                  90                  95

Ala Leu Leu Glu Leu Glu Glu Pro Val Lys Val Ser Ser His Val His
            100                 105                 110

Thr Val Thr Leu Pro Pro Ala Ser Glu Thr Phe Pro Pro Gly Met Pro
            115                 120                 125

Cys Trp Val Thr Gly Trp Gly Asp Val Asp Asn Asp Glu Arg Leu Pro
            130                 135                 140

Pro Pro Phe Pro Leu Lys Gln Val Lys Val Pro Ile Met Glu Asn His
145                 150                 155                 160

Ile Cys Asp Ala Lys Tyr His Leu Gly Ala Tyr Thr Gly Asp Asp Val
                165                 170                 175

Arg Ile Val Arg Asp Asp Met Leu Cys Ala Gly Asn Thr Arg Arg Asp
                180                 185                 190

Ser Cys Gln Gly Asp Ser Gly Gly Pro Leu Val Cys Lys Val Asn Gly
                195                 200                 205

Thr Trp Leu Gln Ala Gly Val Val Ser Trp Gly Glu Gly Cys Ala Gln
            210                 215                 220

Pro Asn Arg Pro Gly Ile Tyr Thr Arg Val Thr Tyr Tyr Leu Asp Trp
225                 230                 235                 240

Ile His His Tyr Val Pro Lys Lys Pro
                245

(2) INFORMATION FOR SEQ ID NO:6:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO:6:

Ile Val Gly Gly Gln Glu Ala Pro Arg Ser Lys Trp Pro Trp Gln Val
 1               5                  10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
            50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Pro Phe Pro
            130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175
```

―continued

```
Asp Asp Met Leu Cys Ala Gly Asn Thr Arg Arg Asp Ser Cys Gln Gly
            180             185             190

Asp Ser Gly Gly Pro Leu Val Cys Lys Val Asn Gly Thr Trp Leu Gln
        195                 200             205

Ala Gly Val Val Ser Trp Gly Glu Gly Cys Ala Gln Pro Asn Arg Pro
    210             215             220

Gly Ile Tyr Thr Arg Val Thr Tyr Tyr Leu Asp Trp Ile His His Tyr
225             230             235             240

Val Pro Lys Lys Pro
            245
```

ENZYMATICALLY-ACTIVE RECOMBINANT HUMAN β-TRYPTASE AND METHOD OF MAKING SAME

FIELD OF THE INVENTION

The invention is directed to a method of making enzymatically-active human β-tryptase in a genetically-engineered microbial host, expression constructs encoding human β-tryptase, and genetically-engineered eukaryotes which express enzymatically-active recombinant human β-tryptase.

BIBLIOGRAPHY

Complete bibliographic citations to the references noted herein are included in the Bibliography section, immediately preceding the Sequence Listing.

DESCRIPTION OF THE PRIOR ART

Human mast cell β-tryptase is a neutral serine protease of presently unknown biological function in vivo. However, it has been implicated in angiogenesis and tissue remodeling. It constitutes up to 20% w/v of the total granule protein of mast cells. β-tryptase is selectively stored in mast cell granules and is released upon mast cell degranulation. Because β-tryptase is unique to mast cells, it has gained favor as a specific marker of mast cell-mediated pathology. For a complete discussion regarding mast cell heterogeneity, structure, and mediators, see Nilsson and Schwartz (1994).

Purified native human β-tryptase is a tetrameric endoprotease of approximately 134 kDa. Each of the four subunits is approximately 31 to 34 kDa in size. As noted in Schwartz (1995), human tryptase was first purified to apparent homogeneity from dispersed and enriched lung mast cells in 1981. However, further research has shown that there are at least two different types, or groups, of human tryptase. These tryptase isoforms are designated herein as α-tryptase and β-tryptase. For purpose of brevity, the unadorned term "tryptase" as used hereinbelow shall refer solely to the β isoform.

Human tryptase is isolated conventionally from cadaveric lung tissue, as described by Smith et al. (1984).

A number of researchers have reported cloning cDNAs which encode human tryptase, see Miller et al. (1990), Vanderslice et al. (1990), and Blom and Hellman (1993), as well as rat mast cell tryptase, see Ide et al. (1995).

However, previous attempts at cloning human tryptase using either bacterial or baculovirus expression systems are plagued with a myriad of problems, including protein folding problems that result in a lack of enzymatic activity. These failures are due, at least in part, to the fact that the tryptase enzyme is extensively modified post-translationally to yield the active form of the enzyme. Consequently, the specific activity of a recombinant tryptase produced in a prokaryote would be expected to be low due to the lack of post-translational glycosylation. As a further consequence, previous attempts to produce enzymatically-active recombinant human tryptase have proven to be far less than ideal because the methods require post-expression chemical modifications to activate the enzyme precursor.

For instance, Sakai et al. (1996) report the expression and purification of recombinant human α-tryptase and β-tryptase precursors in a baculovirus system. However, the tryptase precursors formed are inactive.

Regarding the use of methylotrophic yeasts (e.g., *Hansenula polymorpha, Kluyveromyces lactis, Pichia pastoris, Schizosaccharomyces pombe, Schwanniomyces occidentalis* and *Yarrowia lipolytica*) as hosts for the production of heterologous proteins, the characteristics of these organisms and their suitability for such use has been extensively reviewed in the relevant literature. See, for example, Faber et al. (1995) and Buckholz and Gleeson (1991).

SUMMARY OF THE INVENTION

According to the present invention, DNA encoding human tryptase is cloned, incorporated into a eukaryotic expression vector, and transformed into a suitable eukaryotic host cell. Successfully transformed host cells express, post-translationally process, and secrete enzymatically-active human tryptase. The tryptase so formed has an N-terminal amino acid sequence that is identical to that reported by Vanderslice et al. (1990). Further still, the tryptase produced according to the inventive method has tryptic activity which is comparable to tryptase isolated from cadavers.

In particular, the invention is directed to a DNA expression construct comprising, in 5' to 3' order: a promoter, the promoter operationally linked to a signal sequence, and the signal sequence operationally-linked to a DNA sequence encoding human β-tryptase.

In the preferred embodiment, the DNA expression construct comprises, in 5' to 3' order: a promoter selected from the group consisting of GAP, AOX1, MOX, FMD, ADH, LAC4, XPR2, LEU2, GAM1, PGK1, GAL7, GADPH, CYC1, and CUP1, the promoter operationally linked to a signal sequence, the signal sequence operationally-linked to a DNA sequence encoding human β-tryptase, and the DNA sequence operationally linked to a terminator sequence. Suitable hosts transformed to contain these expression constructs express and secrete enzymatically-active human tryptase.

The invention also is directed to a method of producing enzymatically-active human β-tryptase. The method comprises transforming a yeast host cell with an expression construct as described herein, whereby the host cell expresses enzymatically-active (mature) human β-tryptase. The invention also is directed to the glycosylated tryptase produced and secreted by the transformed host.

A third embodiment of the invention is directed to a genetically-engineered yeast cell which expresses enzymatically-active human β-tryptase. In the preferred embodiment, the genetically engineered yeast cell comprises a *Pichia pastoris* host cell transformed to contain and express an expression construct as described herein.

The invention entails operationally linking DNA sequences that encode the mature form of tryptase immediately downstream (i.e., in the 3' direction) and in-frame to a secretion signal sequence to yield an expression construct. The expression construct, the preferred embodiment of which is a plasmid designated pPIC9-HumTry, then is transformed into a suitable host, preferably a strain of *Pichia pastoris*. Hosts so transformed express and secrete the tryptase encoded by the expression construct. The tryptase expressed is correctly processed by the host cell and secreted into the cell medium as enzymatically-active human tryptase.

Another embodiment of the invention is directed to the enzymatically-active, glycosylated, recombinant protein having tryptase activity which is produced by organisms transformed to contain and express the expression construct.

The invention is further drawn to a method of generating polyclonal or monoclonal anti-human tryptase antibodies comprising inoculating an animal with the enzymatically-active tryptase produced by organisms transformed to contain and express the expression construct. The invention is also drawn to polyclonal or monoclonal anti-human tryptase antibodies produced thereby.

Another embodiment of the invention is a method of screening a substance, such as a chemical compound or mixture of compounds, for its effect on the enzymatic activity of tryptase enzymes. Here, the method comprises contacting the substance with an enzymatically-active recombinant tryptase produced by an organism transformed to contain and express the construct described herein and then measuring the enzymatic activity of the recombinant tryptase.

The invention takes advantage of the fact that native tryptase is synthesized as a proprotein. The modified tryptase amplicon described herein lacks the sequences that encode the N-terminal amino acid prosequence. By cloning this sequence as an in-frame fusion to an N-terminal yeast secretion signal sequence, there is no need to subject the secreted tryptase protein to an activation process. It is secreted as an active enzyme without any further exogenous manipulation required.

To accomplish this result, the signal peptide cleavage site is positioned immediately adjacent to the N-terminus of mature tryptase protein. Cleavage of the signal peptide by action of a host cell protease then removes the signal peptide from the tryptase as it is secreted. The net result is secretion of an enzymatically active, mature form of tryptase containing the same amino terminal residues found in mature native tryptase molecules isolated from human tissues.

A distinct advantage of the method of producing tryptase described herein is that the tryptase so produced does not require any post-expression or post-purification modifications or manipulations to initiate tryptase activity. The tryptase produced according to the invention has enzymatic activity which compares favorably with cadaveric tryptase.

The ready availability of enzymatically-active tryptase afforded by the invention immediately provides previously unattained advantages on several fronts. These include facilitating the large scale screening of combinatorial libraries for specific tryptase inhibitors as potential therapeutics, as well as advancing the understanding of the biological significance of tryptase in mast cell-mediated diseases.

The availability of enzymatically-active recombinant tryptase also offers several advantages over tryptase derived from cadavers. For example, tryptase produced according to the present invention is free of any human pathogens that can be associated with material derived from cadaveric sources.

The method according to the invention can be used to produce large standardized lots (>100 mg) of tryptase having defined specifications.

The quantity of tryptase produced in the preferred Pichia transformant is sufficiently large to enable larger-scale tryptase studies than were possible in the past, such as pharmacological studies, combinatorial library screens, and X-ray crystallographic studies. The large quantity of tryptase produced also allows for the development of tryptase agonists and/or antagonists.

Expression in Pichia also provides a means by which the relationships between tryptase structure and function can be elucidated. Such studies generally utilize a first host wherein the tryptase-encoding DNA is mutagenized and then a second host wherein the peptide encoded by the mutated DNA is expressed. For example, site-directed mutagenesis of tryptase-encoding DNA can be done in conventional *E. coli* hosts, and the mutated DNA then transferred to a suitable eukaryotic host for expression of the novel tryptase.

These and other aims, objects, and advantages of the invention will become apparent upon a complete reading of the following Detailed Description of the Invention and attached claims.

DETAILED DESCRIPTION OF THE INVENTION

Figure 1:
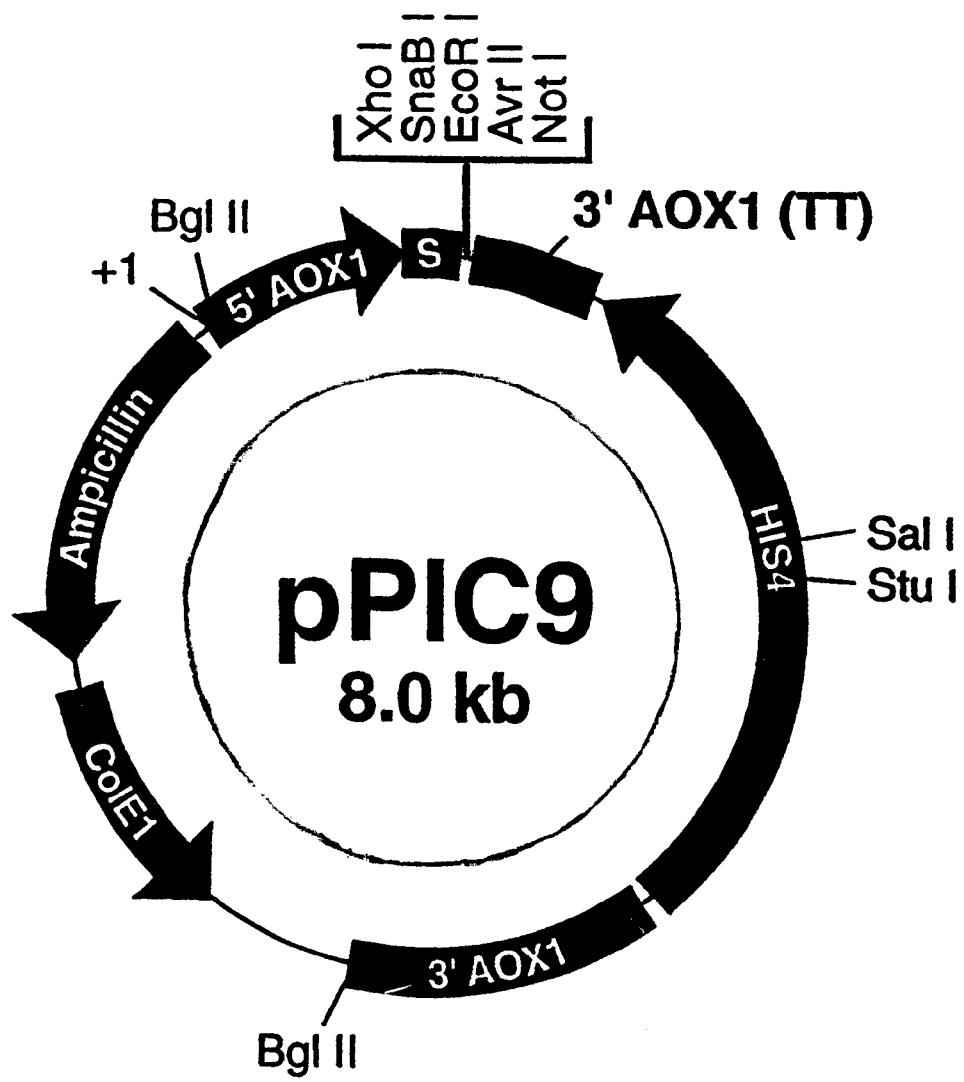
FIG. 1 is a schematic diagram of pPIC9.

Definitions:

To provide a clear and consistent understanding of the specification and claims, the following definitions are used herein. Terms not expressly described have their standard meaning as understood by those skilled in the art.

Enzymatically active—As applied to the expression of heterologous proteins from a genetically-engineered host cell, a protein is enzymatically active when it does not require post-expression or post-isolation chemical processing such as artificial cleavage of a leader peptide or artificial glycosylation in order for the expressed/isolated protein to have the desired activity. Used synonymously with "mature multimeric β-tryptase."

Expression construct—A DNA construct containing at least one sub-sequence encoding a protein or peptide of interest which is operationally linked to one or more regulatory sub-sequences which drive expression of the encoded protein or peptide when the construct is transformed into a suitable host cell. Such constructs also may contain sub-sequences encoding means for selecting host cells transformed to contain the construct, such as sub-sequences which confer antibiotic resistance or dietary limitations to transformed cells.

Host cells—In general, any eukaryote cell amenable to transformation, including, but not limited to, organisms of the genera Hansenula, Kluyveromyces, Pichia, Saccharomyces, Schizosaccharomyces, Schwanniomyces, Yarrowia, and the like, including *Hansenula polymorpha, Kluyveromyces lactis, Pichia pastoris, Saccharomyces cerevisiae, Schizosaccharomyces pombe, Schwanniomyces occidentalis* and *Yarrowia lipolytica.* It is preferred that the host be of the genus Pichia and most preferred that the host cell be a *Pichia pastoris* having the characteristics of ATCC 20864.

Leader peptide—An N-terminal extension of generally from 10 to 85 predominately hydrophobic amino acid residues. The leader peptide initiates a secretory pathway resulting in mobilization of the mature protein out of the cytoplasmic compartment. The leader peptide is cleaved from the mature protein chain post-translation and forms no part of the mature protein. "Leader peptide" is synonymous with the term "signal peptide."

Leader sequence—A DNA sequence located between the transcription start site of an operon and the first structural gene. "Leader sequence" is synonymous with the term "signal sequence." The leader encodes a short peptide called the "leader peptide."

Operationally linked—When referring to joined DNA sequences, denotes that the sequences are in the same reading frame and that upstream regulatory sequences will perform as such in relation to downstream structural sequences. DNA sequences which are operationally linked are not necessarily physically linked directly to one another but may be separated by intervening nucleotides which do not interfere with the operational relationship of the linked sequences.

*Pichia pastoris*—Any strain of the species *Pichia pastoris,* including, but not limited to, those strains having the characteristics of the deposited strains bearing American Type Culture Collection (ATCC, 12301 Parklawn Drive, Rockville, Md. 20852, USA) Accession Numbers 2604, 20864 (synonymous with strain GS115), 28485, 60372, 66390–66395, 76273, and 76274, as well as *Pichia pastoris* strain KM71, available commercially from Invitrogen Corporation (San Diego, Calif., USA). ATCC 20864 (strain GS115) and strain KM71 are the preferred host cell types.

Polymerase Chain Reaction (PCR)—A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction.

Promoter—The DNA sequence site where RNA polymerase binds to the beginning of an operon. A promoter is a DNA sequence that directs the specific transcription of downstream (i.e., 3') DNA sequences into corresponding RNA sequences. A promoter functions as the start signal for RNA synthesis. The promoter itself is not transcribed.

Terminator—A DNA sequence situated at the 3' end of a transcribed sequence that signals the end of transcription.

Tryptase: Unless expressly identified otherwise, human mast cell β-tryptase.

Genetic Engineering:

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described in Sambrook, Fritsch, and Maniatis (1989).

Isolation of Tryptase-Encoding DNA:

DNA sequences encoding human tryptase are isolated by first collecting mast cell samples ($4\times10^6$, 1.1% of total cells) from a human donor. Poly(A)$^+$ RNA is then isolated by LiCl precipitation and oligo(dT)-cellulose chromatography. A cDNA library is constructed in a suitable phage vector (λ ZAP II vector, Stratagene, LaJolla, Calif., USA) and amplified once in *E. coli* XL1-Blue cells prior to screening.

The library is screened at 42° C. with a dog tryptase cDNA labeled to $2\times10^8$ cpm/$\mu$g by nick-translation, in conventional fashion except for using 30% formamide in the hybridization solution. Positive recombinants are identified by autoradiography, plaque-purified, and re-probed. Phagemids containing inserts that hybridize to the cDNA probe are excised from the phage vector using R408 helper phage, transformed into *E. coli* XL1-Blue cells, and purified by alkaline lysis. The sequence of the cDNA inserts can be determined by dideoxy chain termination modified for double-stranded DNA by using "SEQUENASE"-brand sequencing kit (United States Biochemical, Cleveland, Ohio, USA). The M13 forward, reverse, and KS primers (Stratagene) are used for the initial sequence reaction. Subsequent sequencing reactions use oligonucleotide primers designed from the previously determined sequence.

Positive clones can also be used to screen commercial libraries, such as the human placental genomic library in EMBL-3 (Clontech, Palo Alto, Calif., USA). Here, the cDNA is labeled with biotin-7-dATP by nick-translation and hybridized at 50° C. to the immobilized phage DNA and visualized. Positive clones are plaque-purified and re-screened. Phage DNA is purified by the plate lysate method in conventional fashion and digested with BamHI to yield genomic fragments. The genomic fragments are separated by agarose gel electrophoresis, transferred to nitrocellulose, and hybridized to tryptase cDNA. Hybridizing fragments are ligated into the BamHI site of pBluescript KS+phagemid (Stratagene), and the nucleotide sequence determined as described for the cDNAs. See Vanderslice et al. (1990).

A DNA sequence of a tryptase-encoding fragment isolated as described above is depicted in SEQ. ID. NO: 1.

Incorporation of Tryptase DNA Into Expression Construct:

The DNA encoding the tryptase is then operationally linked with suitable regulatory sub-sequences to drive expression of the tryptase-coding sequence in a eukaryotic host, to yield an expression construct. Preferably, the construct also contains one or more sub-sequences to enable the easy identification of postive transformants. At a minimum, the expression construct should include, operationally linked in 5' to 3' order, a promoter sequence, a signal sequence, the tryptase coding sequence, and a terminator sequence. In this fashion, the promoter will initiate transcription of the downstream signal sequence and tryptase structural gene when incorporated into a suitable host.

Several plasmids containing the required regulatory sub-sequences, as well as sub-sequences encoding selectable antibiotic and/or auxotrophic markers and multiple cloning sites are available commercially. A preferred plasmid, pPIC9, is available from Invitrogen (San Diego, Calif., USA). A schematic of pPIC9 is provided in FIG. 1.

pPIC9 is a circular DNA plasmid of 8023 base pairs and contains a 5' AOX1 promoter fragment at bases 1–948, an α-Factor secretion signal (designated S in FIG. 1) at bases 949–1218, a multiple cloning site at bases 1192–1241, and a 3' AOX1 terminator fragment (designated 3' AOX1 (TT)) at bases 1253–1586. pPIC9 also contains an ampicillin resistance gene at bases 7713–6853 and a ColE1 origin at bases 6708–6034. The multiple cloning site includes recognition sites for XhoI, SnaBI, EcoRI, AvrII, and NotI. The plasmid also contains BglII, SacI, SalI, and StuI recognition sites.

Other eukaryotic promoter and terminator sequences can be used with comparable success in the expression construct. Generally, the promoter should be homologous to the chosen host in order to ensure efficient expression of the encoded tryptase, although this is not required. The promoter may be constituitive or inducible. Suitable eukaryotic promoter and terminator sequences include (in addition to AOX1) GAP, MOX, FMD, ADH, LAC4, XPR2, LEU2, GAM1, PGK1, GAL7, GADPH, CYC1, CUP1, and the like. This list is illustrative, not exclusive.

The DNA sequence encoding the tryptase is introduced into the multiple cloning site of pPIC9 by modifying the 5' and 3' ends of the isolated tryptase DNA sequence to yield complementary overhangs with the sticky ends afforded by the restriction sites contained in the multiple cloning site of pPIC9. The pPIC9 plasmid and the amplified tryptase fragments are then digested with suitable restriction enzymes, hybridized, ligated (T4 DNA ligase), transformed (calcium chloride) into a suitable bacterial host (*E. coli* strain JM109, Promega Corporation, Madison, Wis., USA is preferred), and positive clones selected by ampicillin resistance, all in conventional and well-known fashion.

To modify the ends of the tryptase-encoding DNA fragment, the tryptase DNA is amplified using partially homologous nucleotide primers which include suitable restriction nuclease recognition sites but which do not alter the amino acid sequence of the encoded protein. The resulting amplicon thus encodes the same protein, but includes the restriction sites needed to incorporate the tryptase-encoding fragment into an expression construct. Using knowledge of the tryptase DNA sequence and the degeneracy of the DNA code, any number of suitable primers which will introduce an appropriate recognition site without altering the amino acid sequence of the encoded peptide can be constructed.

As described more fully in the Examples, amplifying the DNA sequence as shown in SEQ. ID. NO: 4 with the illustrative primer depicted in SEQ. ID. NO: 2 yields an amplified tryptase-encoding DNA fragment which includes an XhoI restriction site near the 5' end of the fragment and a NotI restriction site near the 3' end of the fragment. These two restriction sites are exemplary only. Virtually any restriction site can be introduced at the terminal ends of the tryptase-encoding DNA fragment without altering the sequence of the encoded tryptase enzyme. The choice is up to the user, and depends almost entirely upon the nature, location, and number of the restriction sites available in the other sub-sequences which are to be incorporated into the ultimate expression construct.

The modified amplicon containing the terminal XhoI and NotI sites can then be easily inserted into any plasmid or construct containing an XhoI recognition site and a NotI recognition site, in conventional and well-known fashion.

Other sub-sequences may also be included in the expression construct. One particularly helpful sub-sequence is a signal sequence encoding a signal peptide to direct the secretion of the expressed protein from the cell. The signal peptide forms no part of the mature protein—the signal peptide is cleaved from the protein as it passes through the cell wall, thereby yielding the mature protein. For purposes of the present invention, the preferred signal sequence is one that encodes a KEX2 cleavage site in the unprocessed protein. The action of KEX2, a yeast signal peptidase, then will cleave the signal peptide from the remainder of the protein, thereby yielding the mature tryptase enzyme. An α-Factor secretion signal sub-sequence is preferred for secretion of the recombinant tryptase using a Pichia host.

After transforming the tryptase-encoding construct into a bacterial host for cloning, positive transformants are screened for the properly assembled expression construct by restriction analysis of plasmids isolated from ampicillin-resistant colonies. The expression constructs are then isolated in standard fashion and transformed into a suitable eukaryotic host for expression of the human tryptase encoded thereon.

Transformation of Eukaryotic Host:

The expression construct encoding human tryptase then is incorporated into a suitable eukaryotic host. The preferred host is a yeast cell. A eukaryotic host must be used so that the expressed tryptase is properly processed by the cell after translation. Post-translational intracellular processing by the eukaryotic host is critical to impart enzymatic activity to the mature protein.

As noted above, the expression constructs can be incorporated into any suitable eukaryotic host, yeast being preferred. The preferred hosts include *Hansenula polymorpha, Kluyveromyces lactis, Pichia pastoris, Saccharomyces cerevisiae, Schizosaccharomyces pombe, Schwanniomyces occidentalis* and *Yarrowia lipolytica*. It is most preferred that the host be of the genus Pichia. From among Pichia, it is most preferred that the host cell be a *Pichia pastoris* cell having the characteristics of ATCC 20864 (strain GS115) or KM71.

Transformation is preferably accomplished by electroporation in conventional fashion. The host cells are made electrocompetent by extensive washing with 1 M Sorbitol and then mixed with aliquots of the expression construct which have been pre-digested with a suitable single-cutting restriction enzyme (e.g., in pPIC9, SalI or SacI) and transformed. Successfully transformed auxotrophs are screened on minimal media, and then rescreened on fresh media to identify clones which produce high levels of tryptase.

If operationally linked to an inducible promoter, successfully transformed auxotrophs are screened in a medium containing the required inducer to initiate tryptase production.

Tryptase can be assayed from the culture broth using an enzyme-linked immunosorbent assay as described in Niles and Haak-Frendscho, U.S. Pat. No. 5,594,116, issued Jan. 14, 1997 and assigned to Promega Corporation, and which is incorporated herein by reference. Briefly, suitable microtiter plates are coated with capture antibodies specific for human tryptase derived from immunized avians, preferably chickens. This is done by coating the microtiter plates with a solution of the capture antibody and incubating for 8 to 48 hours at 4° C. The coated plates are then thoroughly rinsed with a solution of tris-buffered saline with "TWEEN" 20 (TBST). Non-specific residual binding to the microtiter plate itself is then blocked by coating the plate with a blocking buffer. A commonly used blocking buffer is a solution of 0.05% "TWEEN" 20 containing bovine serum albumin (BSA). The plates are again rinsed with TBST.

The solutions to be tested are then diluted in the blocking buffer. Preparing a number of serial dilutions is recommended. The plates are then coated with the test solutions and incubated for at least two hours at room temperature.

After incubation the plates are again rinsed with TBST. Other buffered solutions, such as phosphate-buffered saline or phosphate-buffered saline with "TWEEN," also may be used.

The next step is to introduce a tryptase detect antibody solution which will bind to the captured tryptase. The preferred detect antibody is a murine-derived monoclonal antibody specific to tryptase. A solution of the monoclonal antibody is prepared and the wells are coated and incubated for at least two hours at room temperature. After incubation, the plates are again washed with TBST.

The plates are rinsed with TBST, and are then coated with a conjugate specific antibody/horseradish peroxidase conjugate. Such antibody/horseradish peroxidase conjugates are well known in the art. A conventional method to prepare such conjugates includes using sodium periodate to oxidize the carbohydrate side chains of horseradish peroxidase, followed by the formation of a Schiff base between the activated peroxidase and amino groups of the antibody. The preferred antibody for the conjugate is goat anti-mouse IgG antibodies. The Schiff base then is reduced (sodium borohydride) to yield a stable antibody/enzyme conjugate. The wells of the microtiter plates then are incubated for at least two hours at room temperature. It is important here that the conjugate antibodies must not react with the capture antibody or the tryptase itself. It is preferred that the plates be rinsed with TBS three times prior to addition of the substrate.

A horseradish peroxidase substrate solution is then added to each well and the wells incubated for 15 min at room temperature. Acid is added to stop the color reaction. The wells then are examined spectrophotometrically at 450 nm. For colorimetric detection, horseradish peroxidase-conjugated anti-mouse antibody used in conjunction with the substrate 3,3',5,5'-tetramethylbenzidine (TMB) is preferred. Other peroxidase substrates, such as o-phenylenediamine dihydrochloride (OPD) and anti-mouse alkaline phosphatase conjugates function with equal success. This colorimetric double antibody-sandwich ELISA has a sensitivity of about 20 pg/ml, a linear response range from 15 to 2000 pg/ml, and an r>0.99.

End Uses for Enzymatically-Active Recombinant Human Tryptase:

A distinct advantage of the recombinant human tryptase described herein is that it is enzymatically active. Because the recombinant tryptase is active, it can be used in any application which would otherwise require using a cadaveric tryptase.

For instance, because the recombinant tryptase of the invention has the same biological activity as cadaveric tryptase, it can be used as an antigen to generate anti-human tryptase antibodies in various animals. This is done in well known and conventional fashion by inoculating a test animal, such as a mouse, rat, rabbit, guinea pig, chicken, goat, or other animal, with an initial inoculation of the recombinant tryptase, followed by a series of booster injections. The injections initiate an immunogenic reaction in the animal, resulting in the production of polyclonal antibodies to the recombinant tryptase.

To isolate the antibodies, the IgG fraction of the blood serum (or from egg yolks in the case of avians) is isolated in standard fashion. With egg yolks, this can be accomplished utilizing a commercial product such as Promega Corporation's "EGGstract" TM IgY Purification System (Promega Corporation, Madison, Wis. U.S.A.). There also are a number of other methods for isolating immunoglobulins from serum or egg yolks, such as other sequential precipitation methods, which are well known to those skilled in the field. See, for instance, Scopes, R. K., (1994), "Protein Purification, Principles and Practice," Springer-Verlag: New York. The conventional method of protein isolation, which is completely satisfactory to isolate anti-human tryptase antibodies, is to "salt out" the protein fractions by precipitation of the proteins from a salt solution. The IgY polyclonal antibodies from the serum of the test animal can be isolated using, for instance, chromatographical methods. Again, there are a number of methods well known to those skilled in the art for isolating immunoglobulins from serum or egg yolk samples.

In the same fashion, the recombinant tryptase described herein can be used to generate monoclonal anti-human tryptase antibodies using conventional hybridoma technology. In this technology, a mouse or other test animal is immunized with the recombinant human tryptase to initiate the required immunogenic response. For murine-derived monoclonal antibodies, pristane-primed mice are widely utilized. Spleen cells from the immunized animals are then immortalized by fusion with an immortal cell line, such as a myeloma cell line. The hybrid cells are then serially-diluted, cultured, and screened for those cells which secrete antibodies specific for the recombinant tryptase. The monoclonal antibodies so formed can be used in any number of applications, such as assaying to detect human tryptase, epitope mapping of human tryptase, or for inhibiting tryptase activity for therapeutic or other applications.

The tryptase of the present invention can also be used in drug screening for compounds which act as tryptase inhibitors, antagonists, agonists, etc. For example, like most proteins, the recombinant tryptase can be immobilized on a host of supports, such as the plastic of a microtiter plate. So, to screen for tryptase inhibitors, the recombinant tryptase of the present invention can be coated onto a plastic plate, non-specific binding blocked by washing the plate with bovine serum albumin (BSA), and the plate contacted with a putative tryptase inhibitor. The effectiveness of the inhibitor is then determined by measuring the loss of tryptase enzymatic activity as compared to a standard curve of tryptase activity.

Likewise, the same approach can be used to screen promising drug candidates for their effects on the enzymatic activity of tryptase. This can be done with the recombinant tryptase immobilized on a suitable solid support, as noted above, or in solution phase. Because the subject recombinant tryptase is enzymatically active, the effect of any given compound on the tryptase can be easily determined by measuring the effect the compound has on the enzymatic activity of the tryptase.

The recombinant tryptase can also be used to assay for the presence of tryptase in biological or other solutions. For example, the recombinant tryptase can be used to develop enzyme-linked immunosorbent assays ELISA's for human tryptase. See, for example, U.S. Pat. No. 5,744,319 to Niles and Haak-Frendscho for a description of a double antibody-sandwich ELISA. ELISA's come in many different, but related formats, all of which are exceedingly well known to those skilled in the field. A format widely used due to its relative ease of use and wide linear response range is known as the double antibody-sandwich ELISA. The basic protocol for a double antibody-sandwich ELISA is as follows: A plate is coated with antibodies (called capture antibodies) specific for the immunoglobulin being assayed. In this case, the capture antibodies are polyclonal or monoclonal antibodies specific for the recombinant tryptase which are isolated as described above. The plate then is washed with a blocking agent, such as bovine serum albumin (BSA) to block non-specific binding of immunoglobulins to the test plate. The solution to be tested for the presence of tryptase then is incubated on the plate coated with the capture antibodies. The plate then is washed, incubated with detect antibodies, washed again, and incubated with a specific antibody-enzyme conjugate. After incubation, the unbound conjugate is washed from the plate and enzyme substrate is added. The presence of the bound antibody-enzyme conjugate results in a proportional color change which can be measured and quantified.

For detecting very low levels of tryptase, levels which might be below the detection limit of a given assay, the recombinant tryptase can be used in known quantities (or activities) to spike samples, thereby increasing the concentration of tryptase in the samples being assayed above the detection limit and into the linear response range of the assay being used.

Because the present invention enables the production of large amounts of enzymatically active recombinant tryptase which can be extensively characterized and subjected to quality control measures, antibodies against the recombinant tryptase can be raised and utilized in any number of assay formats to detect the presence of tryptase and to measure the effect of different compounds on the enzymatic activity of tryptase.

EXAMPLES

The following Examples are included solely to provide a more complete understanding of the subject invention. The Examples do not limit the scope of the invention described and claimed herein in any fashion.

Example 1
Construction of pPIC9-HumTry:

The 5' and 3' ends of the human tryptase gene encoded by pBSHumTry (see Vanderslice et al., 1990) were modified via PCR using a pair of partially homologous oligonucleotide primers, SEQ. ID NO: 2 and SEQ. ID NO: 3. The modified tryptase fragment was ligated to the Xho I and Not I sites of pPIC9 (Invitrogen) downstream of the α-Factor secretion signal found on pPIC9 (see "S" in FIG. 1) to yield an expression construct designated pPIC9-HumTry. E. coli strain JM109 (Promega Corporation, Madison, Wis., USA) was transformed with the ligation mix using standard protocols (calcium chloride). Transformants were screened for properly constructed pPIC9-HumTry constructs by restriction analysis of the plasmid DNA isolated from ampicillin-resistant colonies.

Example 2
Transformation of *Pichia pastoris* with pPIC9-HumTry:

Fresh cultures of *Pichia pastoris* strains GS115 (ATCC 20864) and KM71 (Invitrogen) were prepared for electroporation by extensive washing with 1M Sorbitol. Electrocompetent cells were mixed with aliquots of pPIC9-HumTry DNA produced according to Example 1 that had been digested with one of either SalI, BglII, or SacI, and transformed. Transformants were initially identified as His+ prototrophs on minimal media. Methanol utilization phenotypes were analyzed via replica plating on both minimal dextrose and minimal methanol grid plates.

TABLE 1

Media Composition:

| Component | Amount (g) |
|---|---|
| | for Shake Flask (1 L) |
| Calcium sulfate-1H$_2$O | 0.785 |
| Magnesium sulfate-7H$_2$O | 6.11 |
| Ammonium sulfate | 6 |
| EDTA | 0.25 |
| Glycerol | 40 |
| Sulfuric Acid | ~0.85 ml (to pH 2.0) |
| Yeast extract | 1 |
| Antifoam | — |
| DI Water | to 0.885 L |
| Autoclave/Sterilize above components. After cooling, add the following while mixing: | |
| Potassium phosphate, dibasic | 100 ml of a 5.7 g/100 ml autoclaved solution |
| Pichia Trace Minerals | 5 ml |
| Biotin Solution | 10 ml |
| Pichia Trace Minerals (AA1090) | |
| Cupric sulfate-5H$_2$O | 0.78 |
| Sodium iodide | 0.07 |
| Manganese sulfate-H$_2$O | 3.08 |
| Sodium molybdate-2H$_2$O | 0.5 |
| Boric Acid | 0.03 |
| Cobalt chloride-6H$_2$O | 0.8 |
| Zinc chloride | 2.1 |
| Ferrous sulfate-7H$_2$O | 15.0 |
| Sulfuric Acid | 5 ml |
| DI Water | to 1 L |

Filter sterilize.

Example 3
Screening for Tryptase Expression:

Those clones from Example 2 that secreted detectable levels of tryptase were further screened in order to identify those that secreted high levels of tryptase. Cells were grown overnight at 30° C. in 96-well plates in a suitable media. In this Example, the media used was BMGY (buffered minimal glycerol complex media) (commercially available from Invitrogen), the composition of which is listed above in Table 1.

Overnight cultures were transferred to fresh media using a 96-pin inoculating device, then incubated overnight at 30° C. Following a third culture step, the growth of each set of 96 cultures was nearly synchronous. Induction of the synchronized cultures was conducted in 96-well plates containing 200 μl BMMY (buffered minimal methanol complex media) (Invitrogen) per well for 3 days at 30° C. Culture supernatants were sampled each day in order to monitor tryptase accumulation, and to reduce culture volumes for the addition of more methanol. Those clones that excelled at tryptase secretion in 96-well plates were re-screened following induction of the 5 ml cultures.

Figure 2:
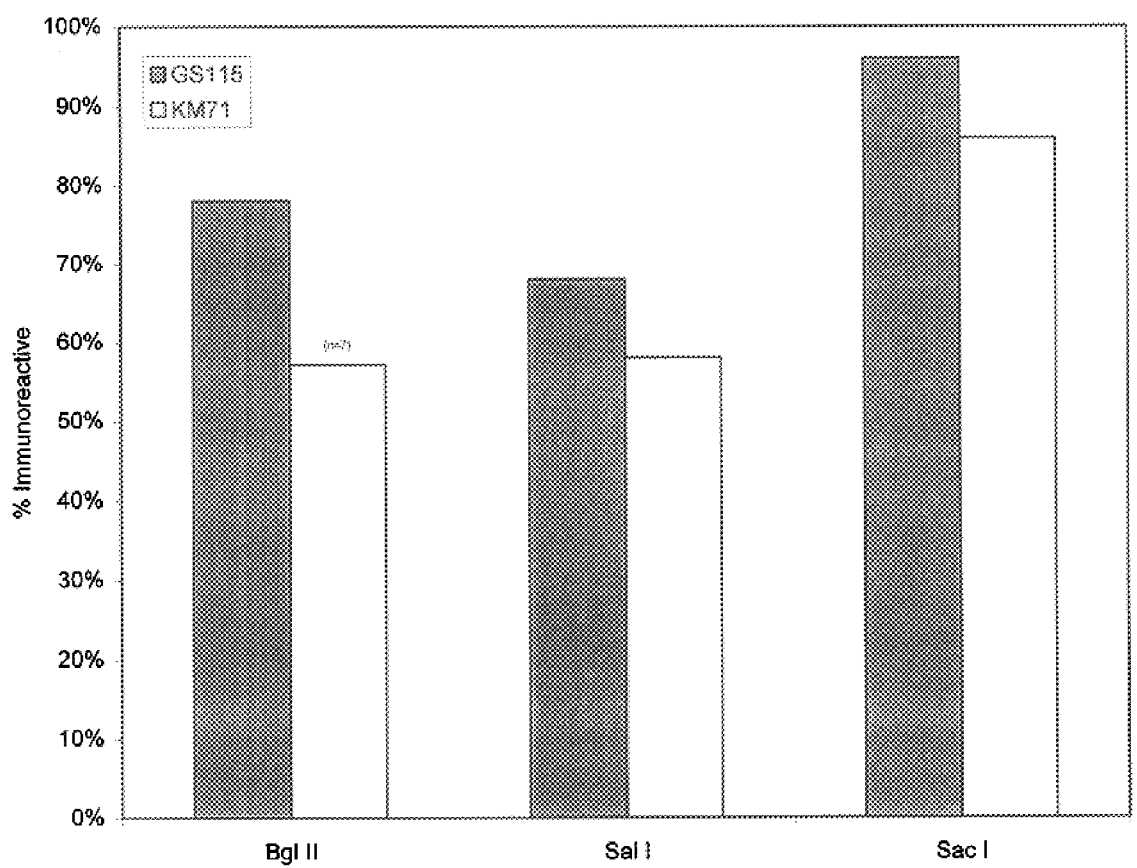
FIG. 2 is a graph depicting the secretion of tryptase from GS115 and KM71 cells transformed to contain pPIC9-HumTry.

The cumulative results of the screening are depicted in FIG. 2. To generate the data presented in FIG. 2, individual transformants were plated on minimal methanol grid plates. Mature colonies were transferred from the grid plates to nitrocellulose filters and screened for secreted tryptase using a modified Western blot protocol (Wung et al. 1996). Filters were sequentially incubated with anti-tryptase IgY (chicken) and goat anti-chicken alkaline phosphatase conjugate. Blots were developed using a NBT/BCIP substrate ("WESTERN BLUE"-brand, Promega Corporation) according to standard protocols. Colonies associated with purple spots were scored as immunoreactive, all others were scored as negative.

Out of the 257 colonies screened in this Example, 197 secreted immunologically detectable levels of tryptase. The fraction of GS115 transformants that secreted tryptase (81%) was slightly larger than for KM71 (71%). However, neither strain exhibited a clear advantage over the other in terms of the yield of productive clones generated from a single transformation. There was also no clear correlation between productive clone yield and integration site (i.e., Bgl II, Sac I, or Sal I).

A GS115 clone that arose from integration of pPIC9-HumTry at the SalI site (i.e., a His+ insertion), was identified as one which secreted high levels of tryptase. This clone, designated GS115/HumTry 5-37, was used for all of the following Examples.

The GS115/HumTry 5-37 clone has been deposited with the American Type Culture Collection, 10801 University Boulevard, Manassas, Va., USA, under Accession No. ATCC 74468, in accordance with the terms of the Budapest Treaty.

Example 4

Fermentation of GS115/HumTry 5-37:

A glycerol stock of the GS115/HumTry 5-37 clone was fermented under standard conditions. Induction was performed under generic conditions known to be suitable for a wide variety of proteins. Supernatants were sampled after 0, 18.5, 26.5, 43.5, 51.5, 67.5, and 73.5 hours of induction. Samples of the fermentation were analyzed by SDS-PAGE, Western blot, and by activity assay.

Figure 3A:
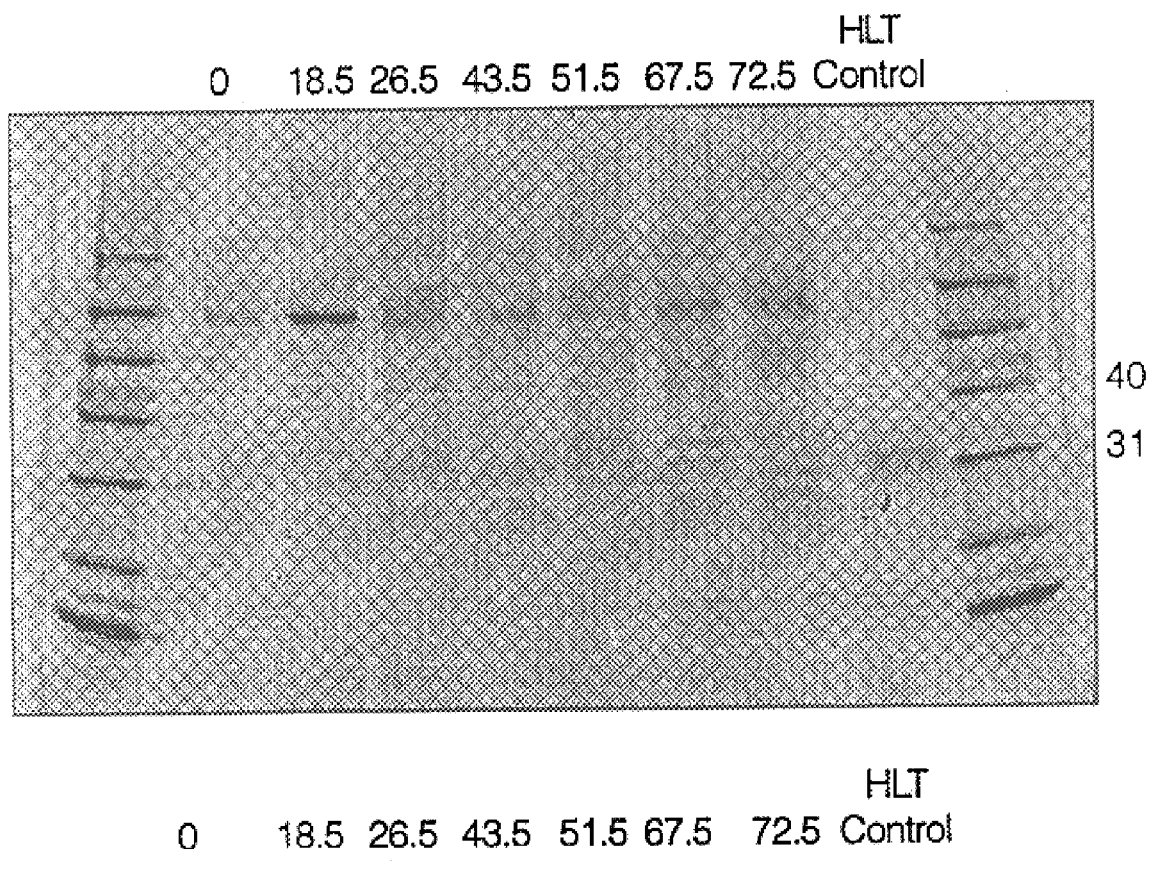
FIG. 3A depicts an electrophoresis gel of culture supernatant from cells transformed to contain pPIC9-HumTry sampled during an induction time course study to evaluate the production of recombinant tryptase after addition of an inducer.

FIG. 3A depicts an electrophoresis gel produced during the induction time course study. To produce this gel, 5 µL samples of each fermentation time point (labelled in hours post-induction in FIG. 3) were loaded onto a 4–20% Tris-glycine reducing gel. Following electrophoresis, the gel was stained with "SYPRO ORANGE"-brand stain (Molecular Probes, Eugene, Oreg., USA) and visualized using a "VISTA FLUORIMAGER" (Molecular Dynamics, Sunnyvalle, Calif., USA). Cadaveric tryptase was included as a control.

As shown in FIG. 3A, prior to induction, only modest levels of tryptase were detectable either by Western blot or enzymatic activity in the fermentation supernatants. Following induction, there was a dramatic increase in both tryptase concentration and tryptase activity. Tryptase accumulation was enhanced by supplementing the BMMY media with 0.5 mg/ml heparin (See Example 5 and FIG. 5). This resulted in nearly linear accumulation of both tryptase and tryptase activity. Prestained molecular weight markers were used as protein size references and mature cadaveric tryptase was used a positive reference control.

Figure 3B:
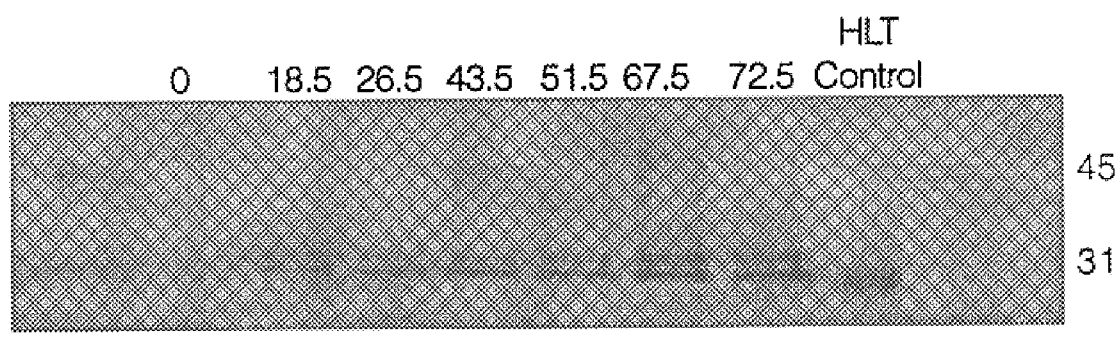
FIG. 3B depicts a Western blot of the electrophoresis gel depicted in FIG. 3A. The gel was visualized by probing with biotinylated anti-human tryptase AA5 monoclonal antibody (Promega Corporation).

FIG. 3B depicts a Western blot of the gel depicted in FIG. 3A. The gel was blotted onto nitrocellulose, blocked with BSA, and probed with a biotinylated anti-human tryptase monoclonal antibody, AA5 (Promega Corporation), to indicate the presence of tryptase. The blots were then incubated with streptavidin-alkaline phosphatase conjugate and developed with nitroblue tetrazolium/5-bromo-4-chloro-3-indolyl phosphate, in conventional fashion. This Western blot clearly shows the increased production of tryptase following induction.

Figure 4:
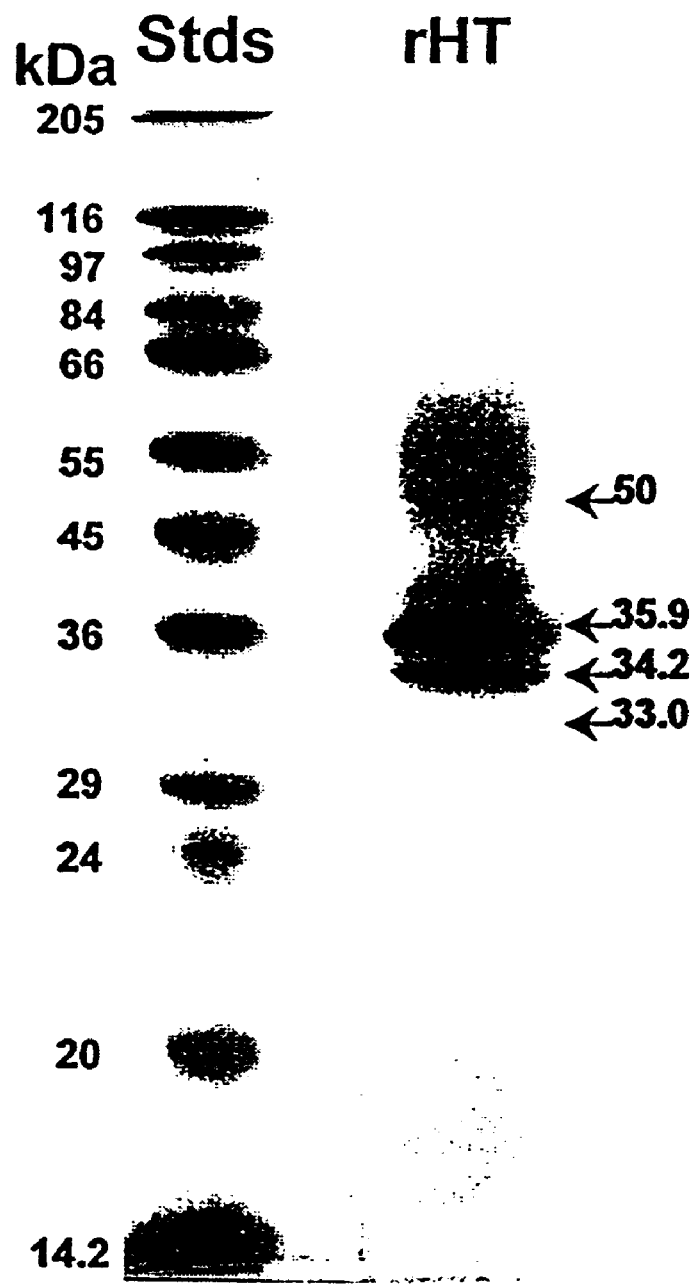
FIG. 4 depicts an electrophoresis gel of culture supernatant from cells transformed to contain pPIC9-HumTry, blotted onto nitrocellulose, blocked with BSA, and probed with a biotinylated anti-human tryptase monoclonal antibody, AA5 (Promega Corporation), to indicate the presence of tryptase. Biotinylated or prestained molecular weight markers were used as protein size references.

Another gel of culture supernate post-induction, run in parallel with biotinylated molecular weight markers, is depicted in FIG. 4. This Western blot was produced and visualized in the same fashion as FIG. 3B.

Example 5

Heparin Stabilization of Secreted Tryptase:

A single GS115/HumTry 5-37 colony was transferred to 200 ml BMGY and grown overnight at 30° C. in shake flasks. Overnight cultures were concentrated by centrifugation and resuspended at an $A_{600}$ of 0.5 in either BMMY or BMMY+0.5 mg/ml heparin. Shake flask inductions were performed at 30° C. for 3 days. Activity assays were performed at 24, 48, and 72 hours postinduction using the N-α-benzoyl-DL-arginine-p-nitroanalide (BAPNA) cleavage assay. The results are presented in FIG. 5.

Figure 5:
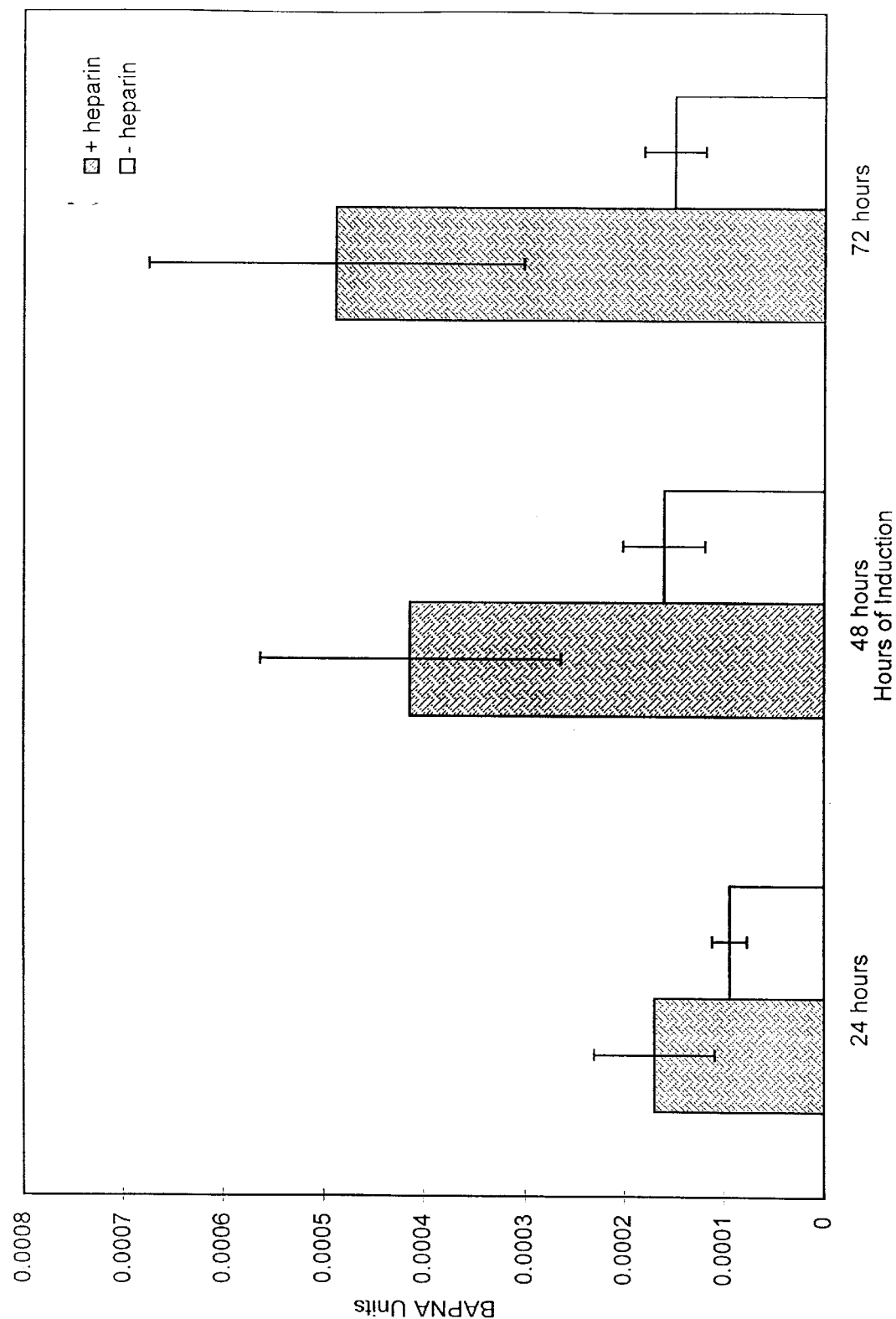
FIG. 5 is a graph depicting heparin stabilization of the recombinant trytase produced according to the present invention.

As shown in FIG. 5, the presence of heparin during induction stabilized tryptase, thereby resulting in increased enzymatic activity.

To generate the data in FIG. 5, supernatants with or without heparin were sampled at 24, 48, and 72 hours post-induction and assayed for activity using BAPNA. Activity of the secreted tryptase was measured by incubating the culture supernatants in 1 mM Tris-HCl (pH 8.0), 1 M glycerol, and 1 mM BAPNA at 37° C. Rates of change in absorbance at 410 nm were monitored for each sample. Relative reaction rates were expressed as the slope of the line plotting the change in absorbance over time (i.e., $\Delta A_{410}/\Delta t$), thereby demonstrating the benefit of exogenous heparin.

Example 6

Glycosidase Treatment:

Aliquots of recombinant human tryptase and cadaveric human lung tryptase were digested with either Endoglycosidase H (Endo H, New England Biolabs, Beverly, Mass., USA) or Peptide N-glycosidase F (PNGase F, New England Biolabs). Each glycosidase treatment contained 10 µg tryptase. Aliquots of each reaction were removed immediately prior to addition of the glycosidase to serve as undigested controls. Detection was by Western blot with anti-human tryptase monoclonal antibody AA5 (Promega). The results indicate that the recombinant protein produced according to the invention is glycosylated (see FIGS. 6 and 7) and the specific activity compares favorable to materials isolated from cadavers.

Figure 6:
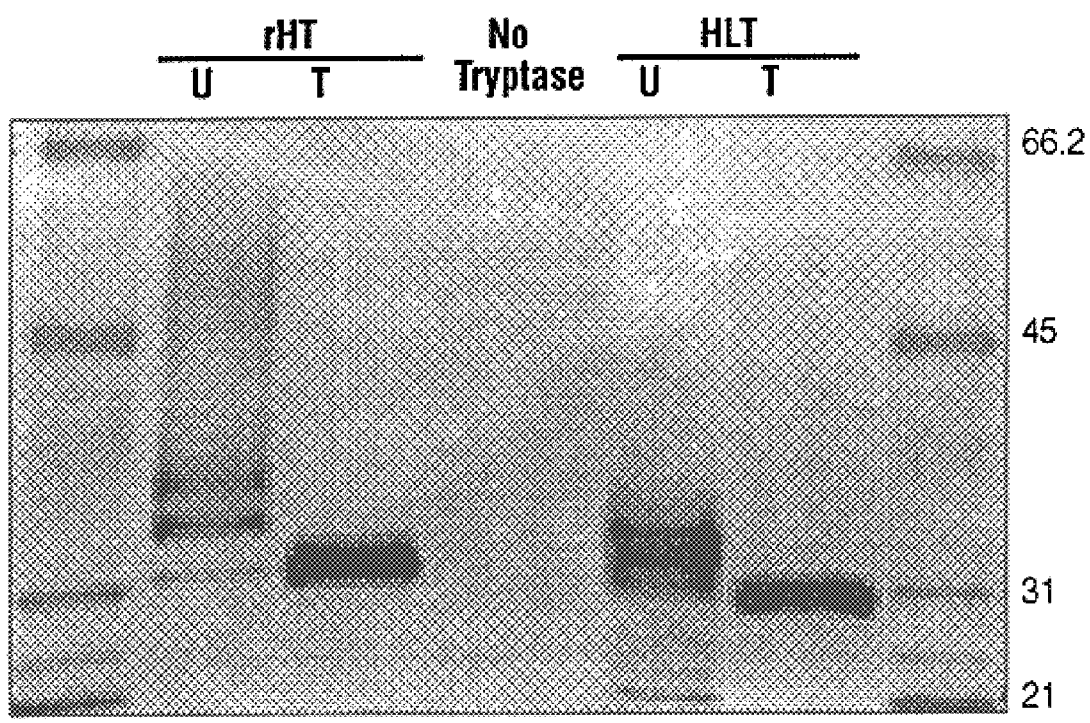
FIG. 6 is a Western blot depicting recombinant human tryptase according to the present invention and cadaveric human lung tryptase before and after digestion with Endoglycosidase H (Endo H, New England Biolabs, Beverly, Mass., USA) and probed with biotinylated AA5 anti-human tryptase monoclonal antibody.
Figure 7:
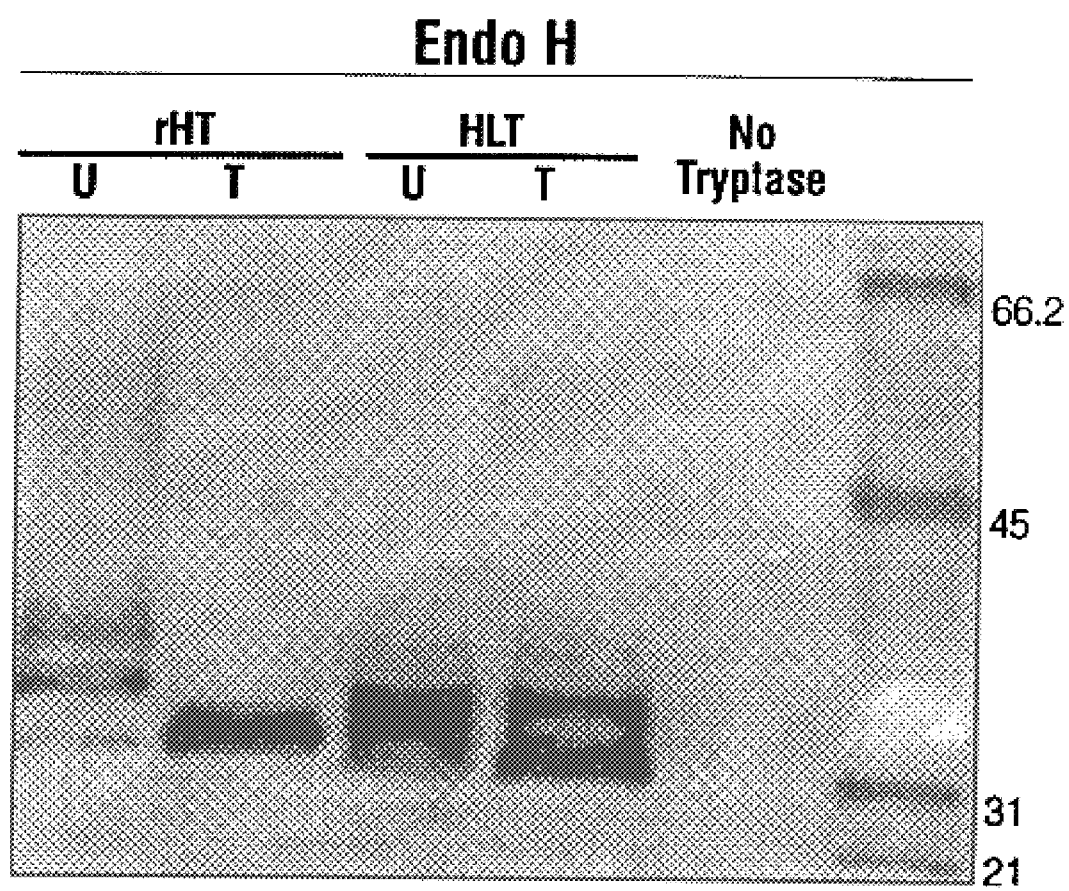
FIG. 7 is a Western blot depicting recombinant human tryptase according to the present invention and cadaveric human lung tryptase before and after digestion with Peptide N-glycosidase F (PNGase F, New England Biolabs).

In FIGS. 6 and 7, the glycosylation of the recombinant human tryptase (rHT) of the subject invention is compared to the glycosylation of cadaveric human lung tryptase (HLT). The lanes marked "U" in FIGS. 6 and 7 are lanes containing recombinant or cadaveric human lung tryptase which were not treated with a glycosidase. The lanes marked "T" contain the corresponding recombinant or cadaveric tryptase after treatement with PNGase F (FIG. 6) or Endo H (FIG. 7). The lanes marked "No Tryptase" are negative controls which do not contain tryptase but do contain glycosidases and all buffers. Protein molecular weight markers are included in the outermost lanes of FIG. 6 and the right-hand lane of FIG. 7.

FIGS. 6 and 7 indicate the presence of three major immunoreactive isoforms of tryptase with apparent molecular weights of 29, 32, and 34 kD. A fourth (apparently minor) isoform migrates as a diffuse smear at about 45 kD. The heterogeneity of the tryptase isoform mixture is reduced to a "core protein" of 29 kD by digestion with either PNGase F or Endo H. (See the columns marked "rHT +" in FIGS. 6 and 7.) Tryptase isolated from natural sources contains at least 4 electrophoretically distinguishable isoforms having apparent molecular weights that range from 29 to 32kD. In the same fashion as the recombinant tryptase, the heterogeneity of the cadaveric tryptase is reduced to a "core protein" of 29 kD following PNGase F digestion (FIG. 6). However, in contrast to the recombinant material, the isoforms present in the cadaveric tryptase are resistant to digestion by Endo H.

Example 7

Purification from Culture Media:

In this Example, the yield and activity of tryptase from a 112 mL sample of media from a fermentation of GS115/HumTry 5-37 is presented. This Example demonstrates the ease of purification and high recovery of tryptase using the subject invention:

TABLE 2

Purification Data from 112 ml conditioned media preparation

| Step | Total Protein ($A_{280}$) | Total Activity (Units) | Specific Activity (Units/mg) | Yield (%) |
|---|---|---|---|---|
| Media: raw supernatant | 3424 | 732 | 0.21 | 100 |
| Butyl HIC resin | 68.7 | 721 | 10.5 | 98.5 |
| Heparin resin | 0.69 | 817 | 1177 | 111 |

Specific activity was determined by TBE assay.

Example 8
Comparision of Kinetics:

In this Example, the kinetics of the recombinant human tryptase according to the present invention (rHT) were compared to the kinetics of cadaveric human lung tryptase (HLT). The results are shown in Table 3:

TABLE 3

Kinetic Data - rHT v. HLT:

| | $K_m$ ($\mu M$) | $k_{cat}$ ($S^{-1}$) | $k_{cat}/K_m$ ($M^{-1} S^{-1}$) |
|---|---|---|---|
| rHT | 67 | 110 | $1.64 \times 10^6$ |
| HLT | 55 | 46 | $0.84 \times 10^6$ |

Example 9
Comparison of Activity:

le;.5qIn this Example, the activity of the recombinant human tryptase according to the present invention (rHT) was compared to the kinetics of cadaveric human lung tryptase (HLT) available commercially from Bioprocessing, Inc ("BPI," Scarborough, Me., USA). Activity was assayed using the BAPNA assay as described above. The results are shown in Table 4:

TABLE 4

Activity: rHT v. Commercially-Available HLT Tryptase:

| Company | Lot # | OD 280/2.81 | Mean Act.(mU/ml) | Specific Act. |
|---|---|---|---|---|
| BPI Tryptase | 04H2897FP | 0.69 | 4.818 | 6,943 |
| rHT | | 0.68 | 6.886 | 10,127 |

Buffer = Tris/glycerol (pH 7.8)

TABLE 4-continued

Activity: rHT v. Commercially-Available HLT Tryptase:

| Company | Lot # | OD 280/2.81 | Mean Act.(mU/ml) | Specific Act. |
|---|---|---|---|---|

Substrate = BAPNA
Samples were diluted 1:50 and 1:100 in buffer

It is understood that the recombinant human tryptase and the methods to obtain the recombinant human tryptase are not confined to the particular reagents, host organisms, and genetic manipulations expressly illustrated and described herein, but embrace all modified and equivalent forms thereof as come within the scope of the attached claims.

BIBLIOGRAPHY

Blom, T. and Hellman, L. (1993), *Scand. J. Immunol.* 37:203–208.

Buckholz, R. G. and Gleeson, M. A. G. (1991), *Biotechnology.* 9:1067–1072.

Faber K. N.; Harder, W.; Ab, G.; and Veenhuis, M. (1995), *Yeast.* 11:1331–1344.

Ide, H.; Itoh, H.; Tomita, M.; Murakumo, Y.; Kobayashi, T.; Maruyama, H.; Osada, Y.; and Nawa, Y. (1995), *J. Biochem.* 118:210–215.

Miller, J. S.; Moxley, G.; and Schwartz, L. B. (1990), *J. Clin. Invest.* 86:864–870.

Nilsson and Schwartz (1994) "Mast-Cell Heterogeneity: Structure and Mediators," Blackwell Scientific Publications, Boston, pp. 195–208.

Sakai K.; Long, S. D.; Dove-Pettit, D. A.; Cabral, G. A.; and Schwartz, L. B. (1996), *Protein Express. & Purif.* 7:67–73.

Sambrook, J.; Fritsch, E. F.; and Maniatis, T. (1989), *Molecular Cloning: A Laboratory Manual;* Cold Spring Harbor Laboratory Press: New York, N.Y.

Schwartz (1995), "Structure and Function of Human Mast Cell Tryptase," *Biological and Molecular Aspects of Mast Cell and Basophil Differentiation and Function,* chapter 14:161–173, Raven Press, Ltd: New York.

Smith, T. J.; Hougland, M. W.; and Johnson, D. A. (1984), *J. Biol. Chem.* 259(17): 11045–11051.

Vanderslice P.; Ballinger, S. M.; Tam, E. K.; Goldstein, S. M.; Craik, C. S.; and Caughey, G. H. (1990), *Biochemistry.* 87:3811–3815.

Wung, J. L. and Gascoigne, R. J. (1996), *BioTechniques.* 21:808–812.

---

What is claimed is:

1. A DNA expression construct comprising, in 5' to 3' order: a promoter, the promoter operationally linked to a signal sequence, the signal sequence operationally-linked to a DNA sequence encoding human β-tryptase, and wherein the expression construct drives the expression of enzymatically-active human β-tryptase in yeast hosts transformed to contain the expression construct, wherein the DNA sequence encoding human β-tryptase is SEQ. ID. NO: 1.

2. The DNA expression construct according to claim 1, wherein the signal sequence encodes a KEX2 cleavage site.

3. The DNA expression construct according to claim 1, wherein the signal sequence includes a 3' terminus encoding amino acid residues Leu-Glu-Lys-Arg.

4. The DNA expression construct according to claim 1, wherein the promoter is a constituitive promoter.

5. The DNA expression construct according to claim 1, wherein the promoter is an inducible promoter.

6. A DNA expression construct comprising, in 5' to 3' order: a promoter selected from the group consisting of AOX1, GAP, MOX, FMD, ADH, LAC4, XPR2, LEU2, GAM1, PGK1, GAL7. GADPH, CYC1, and CUP1, the promoter operationally linked to a signal sequence, the signal sequence operationally-linked to a DNA sequence encoding human β-tryptase, the DNA sequence operationally linked to a terminator sequence, wherein the DNA sequence encoding human β-tryptase is SEQ. ID. NO: 1.

7. The DNA expression construct according to claim 6, wherein the signal sequence encodes a KEX2 cleavage site.

8. A method of producing enzymatically-active human β-tryptase comprising transforming a yeast host cell with an expression construct according to claim 1, wherein the yeast host cell expresses enzymatically-active human β-tryptase.

9. The method according to claim 8, wherein a host cell of the genus Pichia is transformed.

10. The method according to claim 8, wherein a *Pichia pastoris* host cell is transformed.

11. The method according to claim 8, wherein a host cell having the characteristics of *Pichia pastoris* ATCC 20864 or *Pichia pastoris* strain KM71 is transformed.

12. The method according to claim 8, further comprising isolating the enzymatically-active human β-tryptase produced.

13. A genetically-engineered yeast cell which expresses enzymatically-active human β-tryptase comprising a *Pichia pastoris* host cell transformed to contain and express an expression construct according to claim 1.

* * * * *